US005213976A

United States Patent [19]

Blauhut et al.

[11] Patent Number: 5,213,976

[45] Date of Patent: May 25, 1993

[54] PROCESS FOR OBTAINING A POLYHYDROXYALKANOATE FROM THE CELL MATERIAL OF A MICROOGRANISM

[75] Inventors: Wilfried Blauhut; Wolfgang Gierlinger; Friedrich Strempfl, all of Linz, Austria

[73] Assignee: PCD Polymere Gesellschaft m.b.H., Schwechat-Mannswörth, Austria

[21] Appl. No.: 761,244

[22] Filed: Sep. 17, 1991

[30] Foreign Application Priority Data

Oct. 5, 1990 [AT] Austria ................................ 2018/90

[51] Int. Cl.[5] .......................... C12P 7/62; C12N 1/06; C07L 69/66

[52] U.S. Cl. .................................... 435/135; 435/134; 435/136; 435/146; 435/829; 203/14; 203/67; 528/354; 528/361; 528/491; 528/501; 560/185

[58] Field of Search ............... 435/134, 135, 136, 146, 435/829, 872; 528/354, 361, 491, 501; 560/185; 203/67, 14

[56] References Cited

U.S. PATENT DOCUMENTS 3,044,942 7/1962 Baptist .
3,275,610 9/1966 Coty .
4,705,604 11/1987 Vanlantem et al. .................. 203/67
4,786,598 11/1988 Lafferty et al. .
4,910,145 3/1990 Holmes et al. ...................... 435/134
4,957,861 9/1990 Lafferty et al. .
4,968,611 11/1990 Traussnig et al. .
5,110,980 8/1992 Ramsay et al. ..................... 435/146

FOREIGN PATENT DOCUMENTS 0015123 2/1980 European Pat. Off. .
0015669 2/1980 European Pat. Off. .
0046017 7/1981 European Pat. Off. .
0052459 10/1981 European Pat. Off. .
0124309 4/1984 European Pat. Off. .
0168095 6/1985 European Pat. Off. .
0204442 5/1986 European Pat. Off. .
0274151 12/1987 European Pat. Off. .
0288908 4/1988 European Pat. Off. .
0304293 8/1988 European Pat. Off. .

*Primary Examiner*—Herbert J. Lilling
*Attorney, Agent, or Firm*—Wenderoth, Lind & Ponack

[57] ABSTRACT

Process for extracting polyhydroxyalkanoates from the cell material of microorganisms by adding an organic solvent for the polyhydroxyalkanoate which is immiscible with water and which has a boiling point of below 100° C., and, if appropriate, by adding water; stirring the resulting extraction mixture, if appropriate with refluxing; separating off the aqueous phase which contains the cell material in undissolved form from the organic phase; and injecting the organic phase into hot water, causing the dissolved polyhydroxyalkanoate to precipitate and the organic solvent to evaporate, and also isolating the precipitated polyhydroxyalkanoate flocs.

7 Claims, No Drawings

PROCESS FOR OBTAINING A POLYHYDROXYALKANOATE FROM THE CELL MATERIAL OF A MICROOGRANISM

BACKGROUND OF THE INVENTION

The invention relates to a process for obtaining a polyhydroxyalkanoate, synthesized intracellularly by a microorganism, from the cell material, and polyhydroxyalkanoate flocs.

Polyhydroxyalkanoates, in particular homopolymers and copolymers of D-(−)-3-hydroxybutyric acid (poly-HB) are synthesized and accumulated intracellularly by many microorganisms as a storage substance for energy and carbon, and they represent polyesters which have thermoplastic properties and which are biodegradable. Poly-HB can be prepared in good yields with the aid of microorganisms, for example following the procedure described in U.S. Pat. No. 4,786,598 or U.S. Pat. No. 4,957,861. Copolyesters of poly-HB such as, for example, copolyesters which consist of 3-hydroxybutyric acid units and 3-hydroxyvaleric acid units or, alternatively, other acid units, can be prepared by way of fermentation, for example by one of the procedures described in EP-A-0 052 459, EP-A-0 204 442, EP-A0 288 908, EP-A-0 304 293 or EP-A-0 274 151. The polyhydroxyalkanoates formed are integrated into the cell material of the microorganism and must be separated from the cell material, which is relatively difficult. One possible way of separation is extraction with the aid of a solvent, but carrying out the processes described to date also presents difficulties.

For instance, to make the polyhydroxyalkanoate which is integrated in the cell material of the microorganism more accessible to the action of the solvent, it is necessary to provide a separate step for breaking up or solubilizing the cell material upstream of the actual extraction step. For example, U.S. Pat. No.3,044,942 describes pretreatment of the cells with acetone, U.S. Pat. No.3,275,610 describes mechanical pretreatment of the cells by pounding the cells or shaking them with hard objects, EP-A-0,015,123, EP-A-0,124,309 or EP-A-0,168,095 describe spray-drying or pre-drying the microorganism cells in another way, for example by removing the water by means of azeotropic distillation, and EP-A-0,015,669 describes pretreatment of the cells by osmotic shock, ultrasound or lysis of the cell wall. Moreover, the separation of the undissolved cell material which has been pretreated in this manner from the dissolved polyhydroxyalkanoate presents great problems since the undissolved cell material clogs the filters as a jellylike substance, and it is very difficult to remove all the organic phase from the cell material. This is why EP-A-0 046 017 describes flocculation of the cell material before extraction with the aid of a combined alkali, acid and heat treatment to provide better separability, while CA Vol.108, 1988, Ref.73835j proposes the use of a filtering aid such as perlite or diatomaceous earth for separating the cell material from the solvent.

Surprisingly, a simple process has now been found in which there is no need to break up the cells and in which the cell residues can be removed without any complicated procedures and without difficulties, the polyhydroxyalkanoate simultaneously being isolated in the form of flocs which are easy to manipulate and which are surprisingly well suited for further processing into objects.

SUMMARY OF THE INVENTION

The invention therefore relates to a process for obtaining a polyhydroxyalkanoate, synthesized intracellularly by a microorganism, from the cell material of a fermented, aqueous cell suspension, which process is characterised in that at least part of the fermentation solution, or of the water contained in the fermentation solution, is removed from the cell suspension, after which the cell material is treated with an organic solvent for the polyhydroxyalkanoate, which is immiscible with water and which has a boiling point of less than 100° C., with or without the addition of water, whereupon the extraction mixture formed is stirred at temperatures from room temperature to the boiling point of the organic solvent and is allowed to settle, with or without centrifugation, forming an aqueous and an organic phase, and the organic phase which contains the polyhydroxyalkanoate in dissolved form is separated from the aqueous phase which contains the cell residues in undissolved form, whereupon the organic phase is injected into hot water at a temperature which is higher than the boiling point of the organic solvent, causing the organic solvent to evaporate and the polyhydroxyalkanoate to precipitate in the water, the latter being obtained in the customary fashion.

DETAILED DESCRIPTION OF THE PREFERRED EMBODIMENTS

For carrying out the process according to the invention, at least part of the fermentation solution or of the water is first removed from the fermented, aqueous cell suspension. Examples of separation processes which can be employed here are decanting, centrifugation and filtration of the cell material from the fermentation solution, or at least part of the water contained in the fermentation solution is removed by distillation. It is preferred to remove part of the fermentation solution from the cell material by centrifugation, preferably with the aid of a separator. This increases the concentration of the cell suspension, which is important for the rest of the process.

One of the advantages of the process according to the invention is that there is no need to pretreat the cell material by breaking it up or drying it. However, it is also possible to employ pretreated cell material in the process according to the invention.

The cell material, which preferably contains water, or the concentrated cell suspension is treated with an organic solvent for the polyhydroxyalkanoate which is immiscible with water and has a boiling point which is below that of water. Examples of suitable solvents are halogenated hydrocarbons such as methylene chloride, chloroform or trichloroethylene. Methylene chloride is preferably employed. If appropriate, water is also added to the mixture of cell material and organic solvent, since it is essential for optimum phase separation at a later stage that an optimum ratio between cell material, organic solvent and water is formed.

It is preferred to add such an amount of organic solvent and such an amount of water that, after the addition, the ratio by weight of cell material relative to the cell dry weight:water:solvent is approximately 2:1:10 to 1:10:100, particularly preferably approximately 2:3:20 to 1:5:50, very particularly preferably approximately 1:3:20.

The mixture of cell material, organic solvent for the polyhydroxyalkanoate and water is stirred vigorously at temperatures from room temperature to the boiling point of the solvent used. The mixture is preferably stirred with the aid of mixers which allow intensive mixing of the phases, for example with the aid of static mixers or dynamic high-speed stirrers, so as to dissolve the polyhydroxyalkanoate out of the cell material as completely as possible. When high-speed stirrers are used, heating of the solvent is unnecessary, since the polyhydroxyalkanoate is dissolved out of the cell material virtually completely even at room temperature. After thorough mixing and, if appropriate, after cooling, the mixture is allowed to stand, or it is centrifuged, an aqueous and an organic phase being formed. It is preferred to centrifuge the mixture since phase separation is facilitated in this manner. After this the aqueous phase contains the insoluble cell residue, and the organic phase contains the dissolved polyhydroxyalkanoate. To remove the cell material, filtration is unnecessary since the organic phase is separated from the aqueous phase by simple phase separation, the cell residues remaining in the aqueous phase. It is possible that the organic solution obtained is cloudy. To remove the cloudiness, the organic solution can be passed through a deep-bed filter, for example, through a sand bed.

The organic phase which has been separated off and which contains the polyhydroxyalkanoate in dissolved form is subsequently injected into hot water, which has been introduced previously into a container. The temperature of the previously introduced water must be above the boiling point of the organic solvent and below the boiling point of the water, which can also be initially introduced under pressure. To inject the organic phase, all suitable nozzles such as single-component or two-component nozzles of suitable design can be used. It is advantageous to inject the organic phase into the hot water using a two-component nozzle, with the aid of steam as the propellant. As soon as the organic solvent is brought in contact with the initially introduced hot water, the organic solvent evaporates and the polyhydroxyalkanoate precipitates in the initially introduced water in the form of flocs.

Since the initially introduced hot water is cooled by the evaporation of the organic solvent, the water container is advantageously heated, for example with the aid of a heating jacket, and maintained at an approximately constant temperature, and, when steam is used as the propellant, at least part of the heat of evaporation of the solvent is provided by the heat of condensation of the propelling steam.

The amount of the initially introduced hot water is not critical for the success of the procedure. However, it is advantageous to introduce such an amount of water that simple stirring of the content of the receiving vessel prevents settling of the precipitated polyhydroxyalkanoate. This is usually still the case at a polyhydroxyalkanoate concentration of approximately 3%. The organic solvent which has evaporated and the steam which has been entrained according to the prevailing steam pressure are condensed in the customary manner outside the water container. The condensed water can be recycled directly to the water container, and the organic solvent can be reused in a process according to claim 1.

The polyhydroxyalkanoate flocs which have precipitated are subsequently stirred in the hot water for 15 to 60 minutes, preferably 20 to 40 minutes so as to expel the organic solvent as completely as possible, and they are subsequently separated from the water by suitable methods such as filtering, filtering with suction or centrifuging, preferably by centrifuging, and are dried in a suitable manner at temperatures from 60° to 110° C., for example by drying in vacuo or drying in tray ovens. The resulting polyhydroxyalkanoate flocs can be manipulated in an outstanding manner since these flocs contain virtually no dust and allow good flow through the bulk material. Polyhydroxyalkanoates in the form of flocs are novel and also a subject of the present invention. The process can be carried out continuously or batchwise, but it is preferably carried out continuously.

In a preferred embodiment, the poly-HB-containing cell material is separated from the fermentation solution by centrifugation, whereupon such an amount of methylene chloride and, if appropriate, such an amount of water is added to the cell material that the ratio by weight of cell material relative to the cell dry weight:water:methylene chloride is approximately 1:3:10 to 1:5:30. The resulting mixture is either subsequently refluxed for 10 to 60 minutes, with stirring, or stirred at room temperature with the aid of a dynamic high-speed stirrer, and, if appropriate, cooled and centrifuged, in which process an aqueous phase containing the cell residues in undissolved form and an organic phase containing the poly-HB in dissolved form are formed. The methylene chloride phase is withdrawn from the aqueous phase and, with the aid of steam, injected into a heated container into which water has been introduced at a temperature of from 70° to 90° C., with stirring. The poly-HB which is thereby caused to flocculate in the water is stirred in the hot water for 20 to 40 minutes, separated off with the aid of a centrifuge and dried at 80° to 100° C. in a tray oven.

The polyhydroxyalkanoates which are obtained by the process according to the invention can be processed into objects with unexpected ease. For example, injection moulding gave approximately identical cycle periods as in the case of polypropylene. This is entirely surprising to the expert since it is known that polyhydroxyalkanoates crystallize more slowly than polypropylene.

In the above-described fashion, the polyhydroxyalkanoate is separated from the cell material of the microorganism in good yields and in a simple manner, the polyhydroxyalkanoate being obtained in the form of flocs which are easy to manipulate and to process. The process therefore represents an enrichment of the art.

EXAMPLE 1

60 l of an aqueous fermentation solution containing 26% by weight of a cell material of *Alcalicenes latus* with a poly-HB content of 72% by weight, obtained by the procedure described in EP-A-0,144,017 and after removing part of the fermentation solution by centrifugation by means of a disc separator with solids discharge, were treated with 30 l of water and 400 l of methylene chloride and refluxed for 30 minutes with stirring. The resulting mixture was centrifuged at 2200 rpm in a syphon centrifuge with a drum diameter of 630 mm, during which process an aqueous phase containing the cell material of the microorganism in undissolved form and an organic phase containing poly-HB in dissolved form, were formed. The organic bottom phase was withdrawn from the aqueous top phase and injected into 800 l of water at a temperature of 80° C. which had been introduced into a stirred container, by means of a two-component nozzle with a 4 mm diameter bore for the PHB solution and an annular gap width of approx. 2 mm for the propellant, namely steam, at an admission pressure of 3 bar, using a volume stream of 300 l/h. During this process, the temperature of the water was maintained approximately constant with the aid of a heating jacket which surrounded the container. During this process, poly-HB precipitated in the form of flocs, while the methylene chloride and a small amount of the water evaporated and was condensed and collected outside the container. When injecting had ended, the suspension was stirred for 30 minutes at 80° C. The content of the container was subsequently pumped into a trailing-blade centrifuge with a drum diameter of 630 mm, and separated into water and centrifuge-moist poly-HB flocs at a centrifuge speed of 2000 rpm. The centrifuge-moist flocs were dried for 24 hours in a tray drier at 80° C.

This gave 9.5 kg of poly-HB, which is 85% of theory, of a purity of >99% and a methylene chloride content of <1 ppm.

EXAMPLE 2

50 ml of an aqueous fermentation solution as described in Example 1 were treated with 20 ml of water and 350 ml of methylene chloride, and the mixture was stirred for 2 minutes at room temperature with the aid of an Ultra Turrax high-speed stirrer manufactured by IKA, Maschinenbau, Janke & Kunke GmbH, Germany. In this process, 97% by weight of the poly-HB which had been present in the cell material dissolved.

What we claim is:

1. A process for obtaining a polyhydroxyalkanoate, synthesized intracellularly by a microorganism, from the cell material of a fermented, aqueous cell suspension, comprising:

removing at least part of the fermentation solution, or at least part of the water contained in the fermentation solution, from the cell suspension, treating the cell material with an organic solvent to extract the polyhydroxyalkanoate from the cell material, which solvent is immiscible with water and which has a boiling point of less than 100° C., with or without the addition of water, stirring the resulting extraction mixture at a temperature of from room temperature to the boiling point of the organic solvent, allowing the mixture to settle, with or without centrifugation to obtain an aqueous phase and an organic phase, separating the organic phase which contains the polyhydroxyalkanoate in dissolved form from the aqueous phase which contains the cell residues in undissolved form, injecting the organic phase into hot water at a temperature which is higher than the boiling point of the organic solvent, thereby causing the organic solvent to evaporate and the polyhydroxyalkanoate to precipitate in the water in flocs, and isolating the precipitated polyhydroxyalkanoate flocs.

2. The process according to claim 1, wherein the polyhydroxyalkanoate is a homopolymer or copolymer of poly-D(−)-3-hydroxybutyric acid.

3. The process according to claim 1, wherein the at least part of the fermentation solution is removed from the cell suspension by centrifugation.

4. The process according to claim 1, wherein the cell material is treated with an amount of organic solvent and an amount of water so that the ratio by weight of cell material relative to the cell dry weight:water:solvent is from 2:3:20 to 1:5:50.

5. The process according to claim 1, wherein the extraction mixture is centrifuged after stirring.

6. The process according to claim 1, wherein the organic phase is injected into hot water with the aid of steam as a propellant.

7. The process according to claim 1, wherein the precipitated polyhydroxyalkanoate is stirred in the hot water for 20 to 40 minutes.

* * * * *